United States Patent [19]
Dragoo et al.

[11] Patent Number: 6,120,632
[45] Date of Patent: Sep. 19, 2000

[54] METHOD OF MAKING A DIAPER UTILIZING A UNIFORM WIDTH LEG CUFF MATERIAL

[75] Inventors: Jerry L. Dragoo, Fairfield; George S. Reising, Batavia, both of Ohio

[73] Assignee: The Procter & Gamble Company, Cincinnati, Ohio

[21] Appl. No.: 09/182,363

[22] Filed: Oct. 29, 1998

[51] Int. Cl.[7] ............................ A61F 13/49; A61F 13/494
[52] U.S. Cl. .................. 156/164; 156/209; 604/385.01; 604/385.28
[58] Field of Search .................................. 156/163, 164, 156/229, 209, 244; 604/385.01, 385.28, FOR 103, FOR 104, 385.19

[56] References Cited

U.S. PATENT DOCUMENTS

| | | | |
|---|---|---|---|
| 5,554,142 | 9/1996 | Dreier | 604/385.1 |
| 5,653,703 | 8/1997 | Roe | 604/385.1 |

FOREIGN PATENT DOCUMENTS

2287393  9/1995  United Kingdom .

*Primary Examiner*—Adrienne C. Johnstone
*Attorney, Agent, or Firm*—Michael S. Kolodesh; David M. Weirich; Steven W. Miller

[57] ABSTRACT

A method for making an absorbent article having a transverse partition including the following steps: a) providing a first web of barrier leg cuff material having a generally uniform width in a machine direction; b) providing a second webs of barrier leg cuff material in a machine direction generally parallel to the first web of barrier leg cuff material; c) activating at least a portion of said first webs so as to provide an activated region which is extensible in at least said lateral direction; d) providing a transverse partition having a proximal edge and a distal edge; e) joining at least a portion of the transverse partition adjacent the distal edge to the first webs of barrier leg cuff material adjacent to the activated region of the first web of barrier leg cuff material; f) providing a third web of topsheet material; g) joining at least a portion of each of the first and second webs of leg cuff material to the third web of topsheet material; h) providing a fourth web including an absorbent material disposed on a backsheet material; i) joining the third web of topsheet material to the fourth web to form a diaper web; and j) cutting the diaper web into individual absorbent articles.

18 Claims, 5 Drawing Sheets

METHOD OF MAKING A DIAPER UTILIZING A UNIFORM WIDTH LEG CUFF MATERIAL

FIELD OF THE INVENTION

The present invention relates to disposable absorbent articles, and more particularly to methods for making a disposable absorbent article utilizing a uniform width leg cuff material and activating the material to provide a leg cuff of a desired shape.

BACKGROUND OF THE INVENTION

Disposable absorbent articles, such as diapers, are well known in the art. Disposable absorbent articles retain and absorb body exudates, such as urine and fecal material deposited thereon.

Significant advances have been made in the art relative to absorbing and retaining urine deposits. For example, disposable absorbent articles seldom leak and may be relatively thin due to the incorporation of absorbent gelling materials. However, fewer attempts have been made in the art to handle deposits of fecal material in disposable absorbent articles. Fecal material has the undesirable proclivity of smearing onto the wearer's skin, causing epidermal irritation and complicating the task of cleaning the wearer when the soiled diaper or other disposable absorbent article is removed.

To overcome this problem, certain attempts have been made in the art to isolate the fecal material from the skin of the wearer. Such attempts generally provide a void or hole into which the fecal material is deposited and retained. Examples of such attempts are found in U.S. Pat. No. 4,662,877 issued May 5, 1987, to Williams; U.S. Pat. No. 4,892,536 issued Jan. 9, 1990, to DesMarais et al.; U.S. Pat. No. 4,968,312 issued Nov. 6, 1990, to Khan; U.S. Pat. No. 4,990,147 issued Feb. 5, 1991, to Freeland; and U.S. Pat. No. 5,062,840 issued Nov. 5, 1991, to Holt et al.

Attempts have also been made to add a transverse partition to the diaper. The transverse partition limits the migration of fecal material to the front portion of the diaper in which the fecal material is deposited. In some embodiments, the transverse partition is joined with the barrier leg cuffs to ensure containment of fecal material. However, joining a transverse partition to the barrier leg cuffs may hold the cuffs generally over the core and thus reduce the effective distance between the cuffs when in use. Thus, it has been found to be advantageous to provide barrier leg cuffs which are wider in the region of the transverse partition and more narrow in the front and rear waist regions. This configuration provides improved isolation of fecal material without adversely affecting the containment benefits provided by the leg cuffs.

Further, although transverse partition structures have been found to work well as a barrier to limit fecal material migration, they are very difficult to add during high speed manufacture of a diaper. Because transverse partitions generally extend in the cross-machine direction on existing diaper manufacturing lines, the steps necessary to attach the transverse partitions tend to be very complex. Generally, manufacture of a diaper involves multiple operations, virtually all of which occur to a moving web or discrete diaper at very high speeds. Thus, any increase in the number or complexity of operations needed to complete the disposable article adds to the cost. Accordingly, it would be advantageous to provide a method for joining the transverse partition to diaper which is simple and can be done at relatively high speeds.

Therefore, it is an object of this invention to provide a disposable absorbent article having a transverse partition which limits the migration of fecal material within the disposable absorbent article.

It is further an object of this invention to provide a disposable absorbent article having a partition which is readily attachable to upstanding longitudinally oriented barrier leg cuffs.

It is also an object of the present invention to provide a uniform width barrier leg cuff material, yet also, by selectively activating the material, provide barrier leg cuffs which are wider in the region of the transverse partition and more narrow in the front and rear waist regions such that the transverse partition does not adversely affect the containment characteristics of the leg cuffs.

It is a further object of this invention to provide a diaper having a transverse partition which is attached to the upstanding barrier leg cuffs in the commercial manufacturing processes.

It is yet another object of the invention to provide a method of making a disposable absorbent articles having barrier leg cuffs which are wider in the region of the transverse partition and more narrow in the front and rear waist regions such that the transverse partition is held in position by the barrier leg cuffs at the crotch and yet sufficiently removed from the loading zones so as to not adversely affect the containment characteristics of the leg cuffs.

BRIEF SUMMARY OF THE INVENTION

The method of the present invention for making an absorbent article having a transverse partition includes the following steps. First and second webs of barrier leg cuff material of a generally uniform width are provided generally parallel to each other. At least a portion of one of the first and second webs is activated so as to provide an activated region which is extensible in at least said lateral direction. A transverse partition is provided which has a proximal edge and a distal edge. At least a portion of the transverse partition adjacent the distal edge is joined to at least one of the first and second webs of barrier leg cuff material, preferably when the activated region is in an extended condition. A third web of topsheet material is provided and at least a portion of each of the first and second webs of leg cuff material is joined to the third web of topsheet material. A fourth web is provided which includes an absorbent material disposed on a backsheet material. The third web of topsheet material is joined with the fourth web to form a diaper web which may be cut into individual absorbent articles. Alternative embodiments of the invention are contemplated and are described in more detail herein below.

DETAILED DESCRIPTION OF THE INVENTION

As used herein, the term "absorbent article" refers to devices which absorb and contain body exudates and which are placed against or in proximity to the body of a wearer to absorb and contain discharges. The term "disposable" describes absorbent articles generally not intended to be laundered or otherwise restored or reused (i.e., they are intended to be discarded after a single use and preferably recycled, composted, or otherwise disposed of in an environmentally compatible manner). A "unitary" absorbent article refers to an article formed of separate parts united together to form a coordinated entity that does not require separate manipulative parts, like a separate holder and liner. A preferred embodiment of a disposable absorbent article of the present invention is the unitary disposable absorbent article, diaper 20, shown in FIG. 1. As used herein the term "diaper" refers to a disposable absorbent article generally worn by infants and incontinent persons about the lower torso. It should be understood, however, that the present invention is also applicable to other disposable absorbent articles such as incontinence briefs, incontinence undergarments, and diaper holders and liners.

Figure 1:
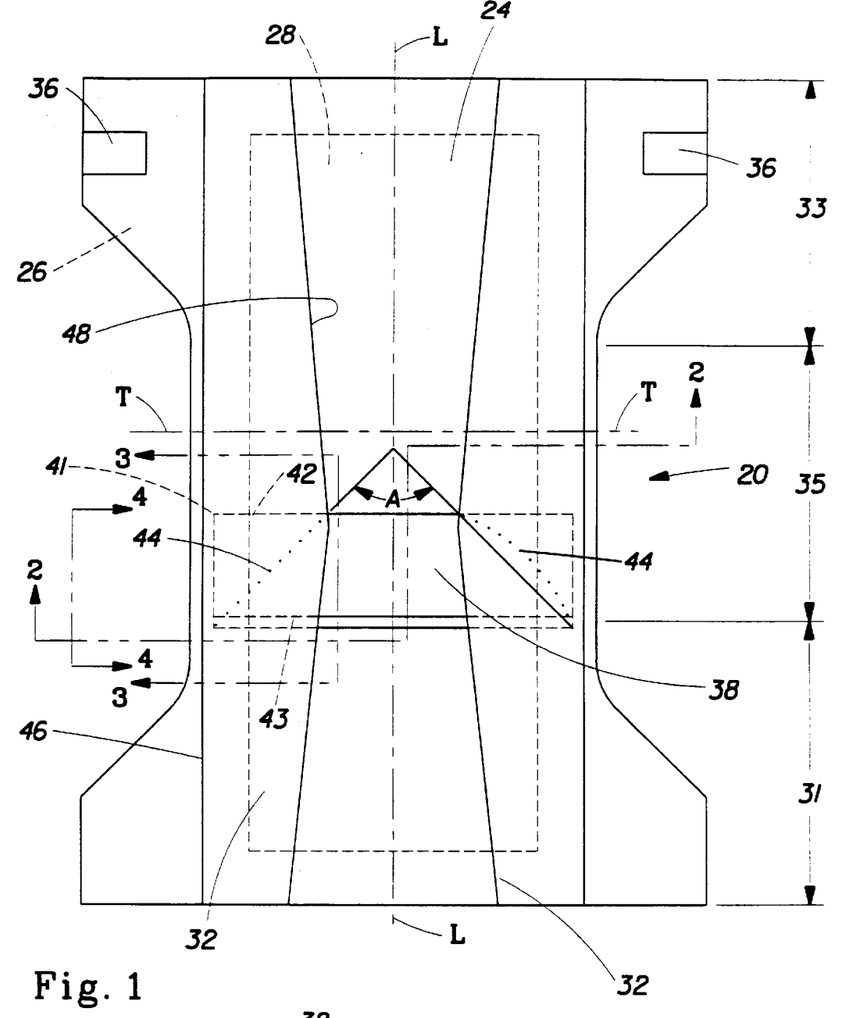
FIG. 1 is a top plan view of the diaper according to the present invention with the body-facing side of the article facing the viewer.

FIG. 1 is a plan view of diaper 20 of the present invention in its flat, uncontracted state (with elastic induced contraction pulled out, and portions of the structure cut away to more clearly show the construction of the diaper 20). The portion of the diaper 20 which faces or contacts the wearer, i.e., the inner surface, is oriented towards the viewer. The diaper 20 has a longitudinal centerline L—L and a transverse centerline T—T. As used herein the longitudinal centerline L—L is aligned front to back and bisects the standing wearer into left and right body halves. The transverse centerline T—T is perpendicular the longitudinal centerline L—L and lies within the plane of the diaper 20. The Z-direction is perpendicular to both the longitudinal and transverse centerlines L—L, T—T and extends outwardly from the plane of the diaper 20.

Figure 2:
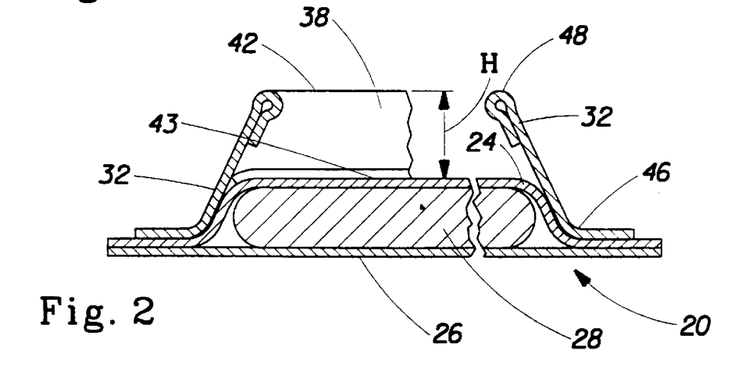
FIG. 2 is an offset vertical sectional view taken along line 2—2 of FIG. 1.

The diaper 20 has a front waist region 31, a rear waist region 33 and a crotch region 35 located between the front and rear waist regions. Further, the diaper 20 includes a chassis comprising a liquid pervious topsheet 24, a liquid impervious backsheet 26 at least partially joined to the topsheet 24, and an absorbent core 28 located between the topsheet 24 and the backsheet 26. (As used herein, the term "joined" refers to the condition where a first member or component is directly affixed or connected to a second member or component where the first member or component is indirectly affixed to the second member or component, or where the first member is directly or indirectly connected to an intermediate member or component which in turn is affixed or connected to the second member or component. Components which are "joined" are intended to remain affixed or connected throughout the intended life of the diaper 20 and not to be separated unless and until the diaper 20 is discarded and as may be necessary for environmentally compatible disposal.) The topsheet 24 has an inwardly oriented surface which is oriented towards the core 28, and an outwardly oriented surface which is oriented towards and/or contacts the wearer. The diaper 20 further comprises a transverse partition 38 attached to the outwardly oriented surface of the topsheet 24 and extending away from the plane of the diaper 20, as illustrated in FIG. 2. The diaper 20 may also include tape fasteners 36 for fastening the diaper 20 about the wearer and an elastic waistband and gasket leg cuffs (not shown). Commonly assigned U.S. Pat. No. 3,848, 594 issued Nov. 19, 1974 to Buell, Re B1 U.S. Pat. No. 4,662,875 reissued May 5, 1987 to Hirotsu et al.; U.S. Pat. No. 5,326,612 issued to Goulait on July 5, 1994; and U.S. Pat. No. 4,963,140 issued to Robertson et al. on Oct. 16, 1990; are incorporated herein by reference to illustrate fasteners 36. U.S. Pat. No. 3,860,003 issued Jan. 14, 1975 to Buell; U.S. Pat. No. 4,081,301 issued Mar. 21, 1978 to Buell; U.S. Pat. No. 4,695,278 issued Sep. 22, 1987 to Lawson; U.S. Pat. No. 4,808,177 issued Feb. 28, 1989 to DesMarais; U.S. Pat. No. 4,795,454 issued to Dragoo on Jan. 3, 1989; and U.S. Pat. No. 4,938,755 issued Jul. 3, 1990 to Foreman, are incorporated herein by reference to illustrate gasket cuffs and barrier leg cuffs 32;. U.S. Pat. No. 4,515, 595 issued May 17, 1985 to Kievit et al.; and U.S. Pat. No. 4,816,025 issued Mar. 28, 1989 to Foreman, are incorporated herein by reference to illustrate elasticized waist features.

The diaper 20 preferably has a pair of upstanding barrier leg cuffs 32, one disposed on each side of the longitudinal centerline L—L. The barrier leg cuffs 32 are generally longitudinally oriented, having a principal direction which is generally parallel to the longitudinal centerline L—L. It will be understood, however, that the barrier leg cuffs 32 may have slight deviations from being parallel to the longitudinal centerline L—L, or may be angled or curvilinear and still be considered longitudinally oriented by one of ordinary skill. Each barrier leg cuff 32 extends outwardly from a proximal end 46. The proximal end 46 is joined to the diaper 20, and preferably is joined to the topsheet 24 of the diaper 20. However, depending upon the exact configuration selected, the proximal end 46 of the barrier leg cuff may be joined to the backsheet 26, or any other component of the diaper 20 without deviation from the invention described and claimed herein. The barrier leg cuff 32 extends from the proximal end 46 to a distal end 48, the distal end 48 being spaced apart from the proximal end 46. Further, the distal end 48 of each barrier leg cuff 32 is spaced apart in the Z-direction from the topsheet 24 in at least a portion of the crotch region when the diaper 20 is in a contracted configuration.

Figure 5:
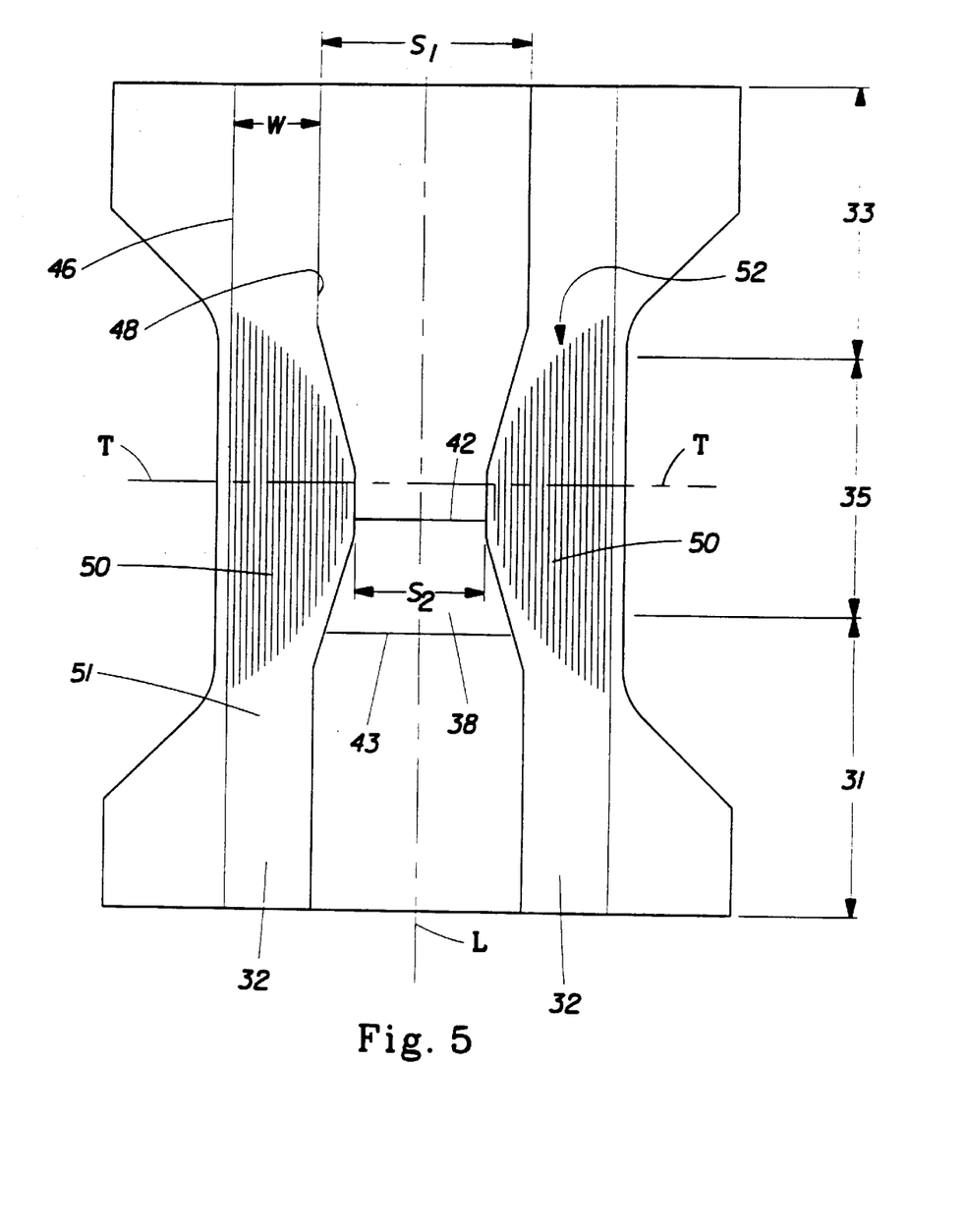
FIG. 5 is a top plan view of the diaper according to the present invention shown partially in cutaway, with the body-facing side of the article facing the viewer.
Figure 6:
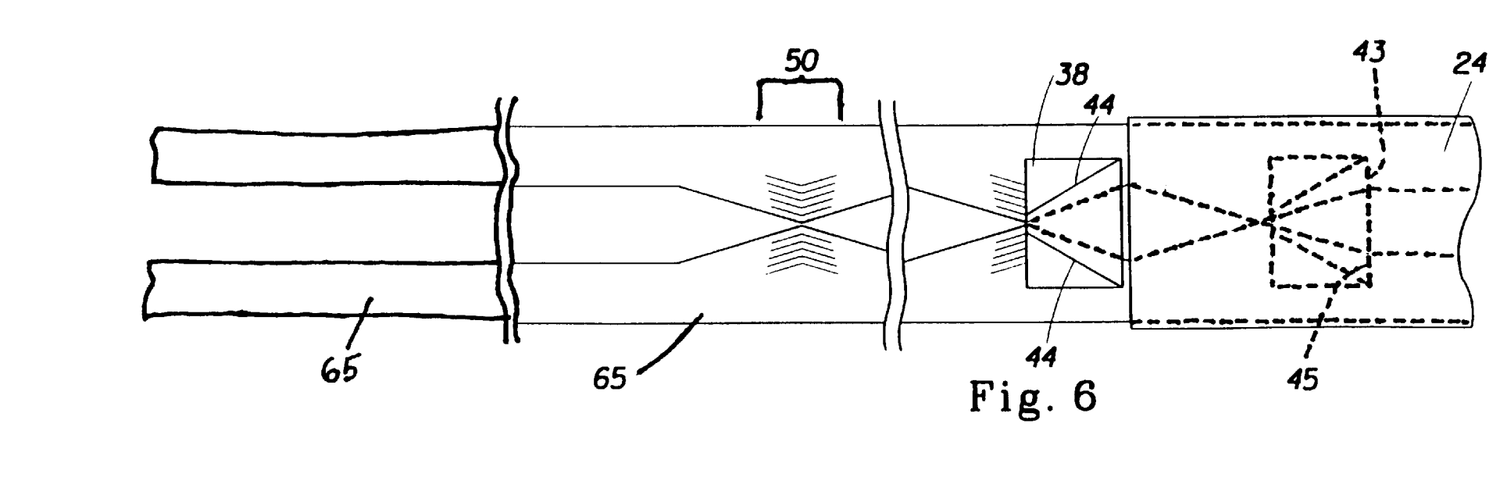
FIG. 6 is a plan view of portions of one method for making the diaper of the present invention.

The barrier leg cuffs 32 are preferably at least partially extensible or elastically extensible, to accommodate the transverse partition 38. It is preferred that the barrier leg cuffs 32 be able to extend in the transverse direction at least adjacent the transverse barrier 38. The lateral extension provides for the proper spacing between the distal edges 48 of the barrier cuffs in the crotch region 35 as well as the waist regions 31 and 33. In one embodiment, the barrier leg cuff material 65 may be provided as a uniform width strip of material as shown in FIG. 6 and then activated such that the material is extensible and/or elastically extensible in at least the area adjacent to the transverse barrier. In an alternative embodiment, portions of the barrier leg cuffs 32 may be folded and tacked down in the front waist region 31, the rear waist region or both to provide the proper spacing. As shown in FIG. 5, in one preferred embodiment, the distance $S_2$ between the distal edges 48 of the cuffs 32 adjacent the transverse barrier 38 is smaller than the distance $S_1$ between the distal edges 48 of the cuffs 32 in the front and/or rear waist regions 31, 33. The width W of the barrier leg cuffs 32 and the spacing between the cuffs is important because cuffs that are too wide can cover too much of the receiving surface of the article while cuffs that are too narrow can permit material deposited onto the article to leak out of the diaper. In one preferred embodiment for medium size babies, the distance $S_1$ is between about 1.0 in and about 4.5 in (about 2.54 cm and about 11.5 cm) and the distance S2 is between about 0.0 in and about 2.0 in (5.1 cm), more preferably between about 0.25 in (0.6 cm) and about 0.75 in (1.9 cm), and most preferably about 0.5 in (1.25 cm).

More preferably, the leg cuffs 32 are elastically extensible in the lateral or transverse direction. (As used herein, the term "elastically extensible" refers to materials that extend in at least one direction when a force is applied and tend to return to approximately their original dimensions after the force is reduced or removed.) In one preferred embodiment, the leg cuffs 32 are elastically extensible throughout their entire length and width. In other embodiments, only portions of the leg cuffs 32 are elastically extensible. In FIG. 5, the region 50 of each leg cuff 32 has been activated to provide elastic extension, and region 51 is a non-activated region of the leg cuff 32. (Although both leg cuffs are shown to have activated regions, the invention will work with only one of the leg cuffs 32 having an activated region 50. The term "activated region" as used herein refers to a zone of a material or element that has been modified to be extensible and/or elastically extensible.) Preferably, the activated region 50 and thus, the elastic extension, is located adjacent the transverse barrier 38. The elastically extensible leg cuffs 32 provide tension on the transverse barrier which helps hold the transverse barrier 38 taut and standing in place when the diaper is worn.

The particular pattern of activation in the activated region 50 of the barrier leg cuffs 32 may provide additional advantages. For example, as shown in FIG. 5, the activated region 50 in each leg cuff 32 may be configured to reduce wrinkling and buckling of the leg cuff 32 once the transverse barrier 38 is added. Since the transverse barrier 38 holds the leg cuffs extended more in at least a portion of the crotch region 35 than in either or both of the waist regions 31 and 33, there will be a transition zone 52 between the more and less extended portions of each barrier leg cuff 32. If the activated region 50 takes on a shape similar to that shown in FIG. 5, the transition zone 52 tends to remain less wrinkled. Although any number of different shaped activation zones 50 may provide the benefit of reducing wrinkling along the transition zone 52, it is generally preferred that the activated region 50 take on a generally triangular, trapezoidal or semicircle shape. The base of the triangle is preferably located close to the proximal edge 46 of the barrier leg cuff 32 and the apex of the triangle is preferably located near or at the point where the distal edge 42 of the transverse barrier 38 is joined to the barrier leg cuff 32.

The activated region 50 may be activated by any means known in the art. Suitable activation methods include addition of elastic or elastic-like elements in the region, cutting, slitting, heating, ultrasonically heating, chemically activating, and/or mechanically activating the material in the activated region 50. One preferred method for activating the activated region 50 of the leg cuffs 32 is to ring roll the material as described in U.S. Pat. No. 5,156,793 entitled "Method for Incrementally Stretching Zero Strain Stretch Laminate Web in a Non-Uniform Manner to Impart a Varying Degree of Elasticity Thereto" issued to Buell, et al. on Oct. 20, 1992; U.S. Pat. No. 5,167,897 entitled "Method for Incrementally Stretching a Zero Strain Stretch Laminate Web to Impart Elasticity Thereto" issued to Weber, et al. on Dec. 1, 1992; and U.S. Pat. No. 5,518,801 entitled "Web Materials Exhibiting Elastic-Like Behavior" issued to Chappell, et al. on May 21, 1996. All of these patents are hereby incorporated by reference herein.

The barrier leg cuffs 32 may be made of any suitable material. In preferred embodiments, the leg cuffs 32 include a hydrophobic nonwoven material, a film, a breathable film, an apertured film, a formed film or combinations thereof. Some preferred embodiments of barrier leg cuffs are described in U.S. Pat. No. 5,151,092 entitled "Absorbent Article With Dynamic Elastic Waist Feature Having A Predisposed Resilient Flexural Hinge" issued to Buell, et al. on Sep. 29, 1992; U.S. Pat. No. 4,695,278 entitled "Absorbent Article Having Dual Cuffs" issued to Lawson on Sep. 22, 1987; U.S. Pat. No. 4,704,115 entitled "Disposable Waist Containment Garment" issued to Buell on Nov. 3, 1987; all of which are hereby incorporated by reference herein.

The topsheet 24 and backsheet 26 of the diaper 20 have longitudinal and transverse dimensions generally larger than those of the absorbent core 28, so that the topsheet 24 and backsheet 26 may extend beyond the core 28 to thereby form the periphery of the diaper 20. The embodiment described herein is suitable for a wearer weighing about 2.5 to about 12.7 kilograms (about 5 to about 28 pounds). It will be understood, however, that if the diaper 20 is intended for use with larger or smaller wearers, including adults, the diaper 20 should be scaled accordingly.

The topsheet 24 may comprise any liquid pervious facing of the diaper 20 which contacts the skin of the wearer and prevents substantial contact of the absorbent core 28 with the skin of the wearer. The topsheet 24 is preferably compliant, aesthetically pleasant, and non-irritating to the skin. A suitable topsheet 24 may be manufactured from porous foams, apertured plastic films, natural fibers, synthetic fibers, or a combination thereof One preferred topsheet 24 comprises polypropylene fibers and may be manufactured as a nonwoven web of spunbonded, carded, wet laid, melt blown, hydroentangled fibers. Such a preferred topsheet 24 may be carded and thermally bonded to have a basis weight of 14 to 25 grams per square meter. An example of one suitable topsheet 24 is marketed by Veratec Inc., Division of International Paper Company, of Walpole, Mass. under the designation P-8. Another preferred topsheet includes an apertured formed film such as "DRY WEAVE" marketed by Procter & Gamble.

The backsheet 26 is preferably hydrophobic or impervious to fluids such as urine and prevents fluids absorbed and contained by the core 28 from wetting the wearer's undergarments. As used herein, the "backsheet" refers to any partition disposed outwardly of the core 28 as the diaper 20 is worn and which contains absorbed liquid within the diaper 20. The backsheet 26 is preferably manufactured from a thin plastic film, although other flexible, liquid impervious materials may be used. As used herein, the term "flexible" refers to materials which are compliant and will readily conform to the general shape of the human body. The backsheet 26 may be a polyolefinic film, such as polyethylene, having a thickness of about 0.002 to 0.005 cm. A suitable backsheet 26 can be made from a blend of 45 to 90 percent LLDP and about 10 to 55 percent polypropylene. Exemplary backsheet films are sold by Tredegar Industries of Terre Haute, Ind. under the designation RR8220 and RR5475. Alternatively, the backsheet 26 may include breathable and/or clothlike materials that permit vapors to pass through but still prevent liquids from leaking out of the diaper 20.

The topsheet 24 and backsheet 26 are generally coextensive and at least partially peripherally joined. The topsheet 24 and backsheet 26 may be joined by any means well known in the art, such as adhesive bonding or heat sealing. A particularly preferred method of joining the topsheet 24 and backsheet 26 is with hot melt adhesives such as are manufactured by Century Adhesives, Inc. of Columbus, Ohio and marketed as Century 5227, or BL1258 adhesive sold by the H.B. Fuller Company of St. Paul, Minn. Another example is available from the Findley Adhesives Company of Elmgrove, Wis. under the trade designation H2031.

The diaper 20 preferably includes an absorbent core 28 disposed between the topsheet 24 and the backsheet 26 in at least a portion of the crotch region 35. (As used herein, the term "core" refers to any component of the diaper 20 used for absorbing and retaining body exudates.) The absorbent core 28 may be made from a variety of materials such as comminuted wood pulp and may further contain particulate or fibrous absorbent gelling materials as are commonly known in the art. The absorbent core 28 may be made in accordance with the teachings of commonly assigned U.S. Pat. No. 4,610,678 issued Sep. 9, 1986 to Weisman et al.; U.S. Pat. No. 5,137,537 issued Aug. 11, 1992 to Herron et al.; and U.S. Pat. No. 5,147,345 issued Sep. 15, 1992 to Young et al., which patents are incorporated herein by reference. Absorbent gelling materials, if desired, may be made in accordance with commonly assigned U.S. Pat. No. Re. 32,649, reissued Apr. 19, 1988 to Brandt et al., and which is incorporated herein by reference. The core 28 may be encased by one or more layers of tissue.

Spanning at least a portion of the transverse dimension of the diaper 20 is an upstanding transverse partition 38. The transverse partition 38 is generally transversely oriented. By generally transversely oriented, it is meant that the transverse partition 38 is substantially parallel to the transverse direction T—T of the diaper 20. It is to be recognized that the transverse partition 38 may be angled or curvilinear and still be considered transversely oriented by one of ordinary skill. If the diaper 20 has barrier leg cuffs 32, preferably the transverse partition 38 spans the entire distance between the barrier leg cuffs 32. The transverse partition 38 has two side edges 41, the side edges 41 being spaced apart in the transverse direction. The transverse partition 38 may be generally made according to the teachings of commonly assigned U.S. Pat. No. 5,554,142, issued Sep. 10, 1996 to Dreier et al., the disclosure of which is incorporated herein by reference.

The transverse partition 38 is joined to the diaper 20, and preferably to the topsheet 24 of the diaper 20, at a proximal end 43. It will be understood by one of ordinary skill that various other constructions wherein the proximal end 43 of the transverse partition 38 is joined to other components of the diaper 20, such as the backsheet 26 or core 28, are feasible and do not deviate from the scope of the invention described and claimed herein.

The transverse partition 38 is preferably joined to each of the barrier leg cuffs 32. The transverse partition 38 is preferably joined to each of the barrier leg cuffs 32 adjacent at least a portion of the distal edges 42 of the transverse barrier 38. The transverse barrier 38 is preferably also joined to the topsheet 24 adjacent at least a portion of the transverse barrier proximal edge 43. By joining the transverse partition 38 to the barrier leg cuffs 32 and the topsheet 24, an H-shaped pattern is formed including the barrier leg cuff 32 and the transverse partition 38. This H-shaped pattern prevents fecal material deposited in the rear portion 33 of the diaper 20 from migrating to the front portion 31 of the diaper 20. By containing the fecal material in the rear portion 33 of the diaper 20, the cleaning task becomes easier for the caretaker. Further, the fecal material is contained to a smaller area and is kept away from the genitals of the wearer.

The transverse partition 38 is preferably disposed on the body facing surface of the topsheet 24 and extends outwardly therefrom to present an abrupt discontinuity in the body facing surface of the topsheet 24. The transverse partition 38 obstructs the longitudinal migration of fecal material deposited in the rear waist region 33 of the diaper 20 from migrating towards the front waist region 31 of the diaper 20. The transverse partition 38 may vary in size and shape from that which is shown herein, but in any case is preferably parallel to the transverse centerline T—T of the diaper 20. If desired, the transverse partition 38 may even be coincident with the transverse centerline T—T of the diaper 20.

The transverse partition 38 extends outwardly from the plane of the diaper 20, with a vector component in the Z-direction, to a distal edge 42. It is important that the transverse partition 38 be upstanding when the diaper is fitted to a wearer and rise in the Z-direction above the plane of the outwardly oriented surface of the topsheet 24 to an effective height H spaced from the plane. The effective height H should be sufficient to present an abrupt discontinuity in order to obstruct the longitudinal movement of fecal material. It is to be recognized that if the topsheet 24 has wrinkles, rugosities, undulations, or other deviations from planarity, these should be taken into account at the position of the distal edge 42 of the transverse partition 38 when determining its effective height H. Otherwise such deviations from planarity in the topsheet 24 may diminish the effective height H of the distal edge 42 of the partition 38 above the topsheet 24, and not sufficiently obstruct the movement of fecal material.

As used herein, the "effective height" is the Z-direction distance from the plane of the outwardly oriented surface of the topsheet 24 to the distal edge 42 of the transverse partition 38. The effective height H is measured in the Z-direction while the diaper 20 rests on a horizontal surface, allowing elastic induced contraction to occur, thereby simulating the in-use condition. The distal edge 42 of the transverse partition 38 preferably has an effective height H above the body facing surface of the topsheet 24 of between 1.5 centimeters and 6.0 centimeters, and most preferably about 4.5 centimeters.

Figure 3:
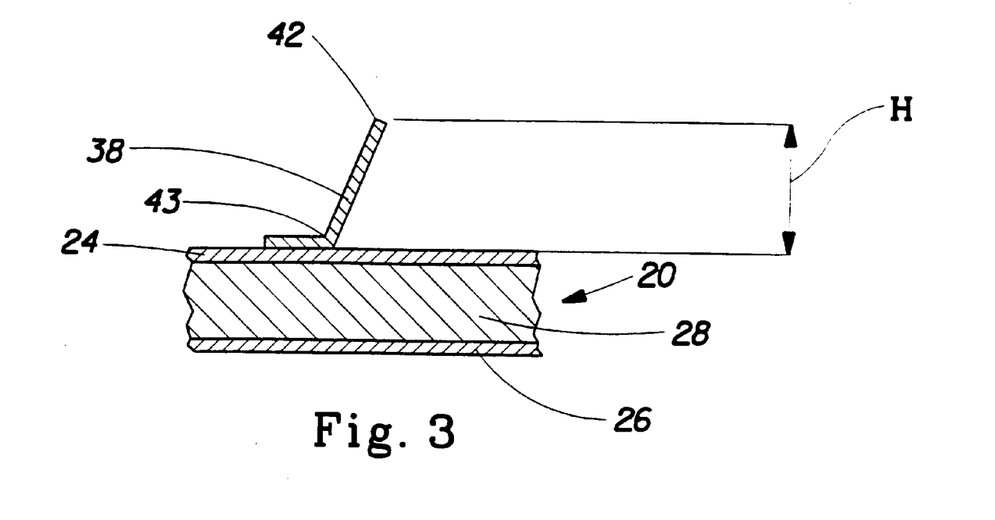
FIG. 3 is a vertical sectional view taken along line 3—3 of FIG. 1.

As illustrated in FIG. 3, the transverse partition 38 may be disposed in an angular relationship to the plane of the diaper 20 so that the distal edge 42 of the upstanding transverse partition 38 is oriented toward the rear waist region of the diaper 20. Alternatively, the transverse partition 38 may be perpendicular to the plane of the diaper 20. The angled arrangement provides the advantage that the pressure of fecal material deposited in the diaper helps seal the transverse partition 38 against the wearer's body, minimizing the leakage of fecal material across the transverse partition 38. The arrangement further minimizes the vertical forces necessary to maintain the transverse partition 38 in contact with the body of the wearer.

The transverse partition 38 may be made of a urine pervious material, but is preferably made of a material impervious to runny BM. In one embodiment, the transverse partition 38 is impervious to fecal material but at least partially pervious to urine. The impervious material prevents (or minimizes the amount of) runny fecal material from reaching the genitalia of the wearer. Suitable materials for the transverse partition 38 include breathable composite laminates, elongated films, nonwoven materials, and laminates thereof If a laminate material is used, it is preferred that the more skin friendly surface of the laminate be oriented toward the wearer. Suitable materials for the transverse partition 38 include foams, formed films, scrims and laminates thereof In yet other preferred embodiments, the transverse partition 38 may include a material that permits urine to pass through but is resistant to runny feces. Apertured formed film such as "DRY WEAVE" marketed by Procter & Gamble are also suitable as are other materials which permit liquids to pass in one direction but generally inhibit liquids and solids from passing in the opposite direction.

Preferably, the transverse partition 38 is joined to each of the barrier leg cuffs 32 at lines of attachment 44. The lines of attachment 44 have a projection onto the plane of the diaper 20. The projection of the lines of attachment 44 onto the plane of the diaper 20 are preferably divergent as one of the waist margins is approached. As illustrated in FIG. 1, the lines of attachment 44 preferably diverge as the front waist margin is approached. A pattern which diverges towards the front waist margin is preferred over a pattern which diverges towards the rear waist margin because the barrier leg cuffs 32 are closest to each other and to the longitudinal centerline L—L at the distal edge 42 of the transverse partition 38. Further disclosure related to the lines of attachment can be found in U.S. patent application Ser. No. 08/722,731 filed on Oct. 1, 1996 in the names of Dragoo et al., which is incorporated by reference herein.

Alternatively, the lines of attachment 44 may be thought of as being disposed in a skewed, i.e., non-parallel, relationship to the longitudinal centerline L—L. A line of attachment 44 is considered skewed relative to the longitudinal centerline L—L if the theoretical extension of the line of attachment 44, in either longitudinal direction intersects the longitudinal centerline L—L, when the line of attachment 44 is projected onto the plane of the diaper 20. Preferably, the line of attachment 44 diverges away from the longitudinal centerline L—L as the front waist region 31 of the diaper 20 is approached.

Figure 4:
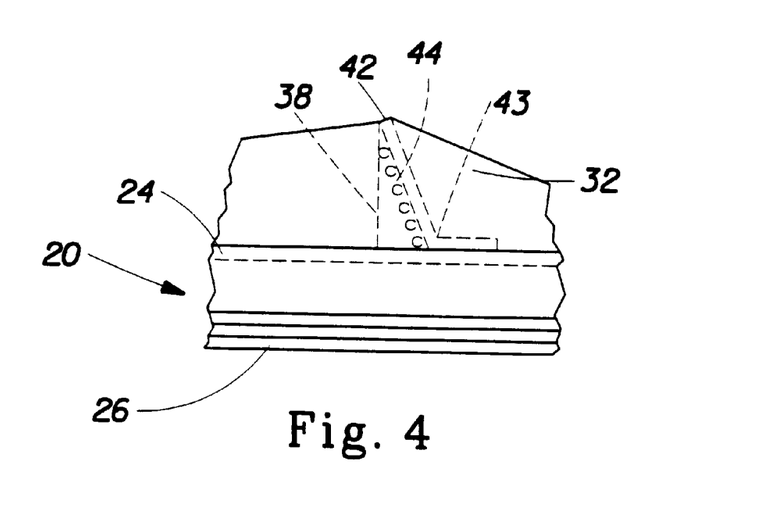
FIG. 4 is a fragmentary side elevational view taken along line 4—4 of FIG. 1.

Referring to FIG. 4, the transverse partition 38 may be attached to the barrier leg cuffs 32 by any joining means which is well known in the art. Suitable joining means include heat sealing, adhesive joining, ultrasonic welding, and autogenous bonding. A preferred autogenous bonding technique is disclosed in commonly assigned U.S. Pat. No. 4,919,738, issued Apr. 24, 1990 to Ball et al., the disclosure of which is incorporated herein by reference.

The line of attachment 44 may comprise either discrete bond sites or a continuous bond. Discrete bond sites may be preferred because the resulting diaper 20 is generally more flexible, and hence more comfortable to the user than a like diaper 20 made with a continuously bonded line of attachment. However, if discrete bond sites are selected for the lines of attachment 44, the discrete bond sites should not be spaced so far apart that fecal material, particularly low viscosity fecal material, can pass between the discrete bond sites and enter the front portion 31 of the diaper 20.

The lines of attachment 44 are preferably rectilinear, although the lines of attachment 44 may be curvilinear. If curvilinear lines of attachment 44 are selected, the curvilinear lines of attachment 44 are preferably concave towards the longitudinal centerline L—L in order to maximize the volume available for fecal material to occupy. If curvilinear lines of attachment 44 are selected, preferably the curvilinear lines of attachment 44 are generally circular and have a radius of curvature which is approximates the length of the proximal edge 43 of the transverse partition 38.

Referring to FIG. 1, the lines of attachment 44 are projectable onto the plane of the diaper 20. When the lines of attachment 44 are projected onto the plane of the diaper 20, the theoretical extension of the lines of attachment 44 form an included angle A. Each of the lines of attachment 44 forms one ray of included angle A. Preferably, the longitudinal centerline L—L bisects included angle A. If the lines of attachment 44 are curvilinear, the theoretical extension between the extremities of the principal portions of the lines of attachment 44 are used in determining the projection onto the plane of the diaper 20. The included angle A may range from 60 to 150 degrees, and preferably ranges from about 70 to 130 degrees, and from 80 to 100 degrees.

Multiple and even parallel bond sites may be utilized to join the transverse partition 38 to each of the upstanding barrier leg cuffs 32. If such an arrangement is selected, the lines of attachment 44 projected onto the plane of the diaper 20 are those lines of attachment 44 which control the position of the transverse partition 38 relative to the barrier leg cuffs 32. Generally, but not necessarily, the lines of attachment 44 which are disposed nearest the longitudinal centerline L—L of the diaper 20 are controlling and should be used in determining included angle A. If it cannot be determined which discrete bond sites form the controlling lines of attachment 44, or if multiple lines of attachment 44 control the attachment of the transverse partition 38 to the barrier leg cuffs 32, then any projection of any combination of lines of attachment 44 onto the plane of the diaper 20 may be utilized in determining included angle A.

The included angle A between the lines of attachment 44 will necessarily change as the angular relationship between the transverse partition 38 and the topsheet 24 changes. The concluded angle A will also change to accommodate differences in the length of the transverse partition 38 or differences in the effective height H of the transverse partition 38. Generally, as the effective height H of the transverse partition 38 increases and the angular relationship between the transverse partition 38 and the topsheet 24 remains constant, the included angle A of the lines of attachment 44 should remain constant. As the length, in the transverse dimension, of the transverse partition 38 increases measured at its proximal edge 43, the included angle A between the lines of attachment 44 should generally decrease. Also, as the angle between the transverse partition 38 and the topsheet 24 approaches 90 degrees, i.e., the transverse partition 38 becomes more perpendicular to the topsheet 24, the included angle A between the lines of attachment 44 should increase. Such changes are necessary to assure that the transverse partition 38 does not restrict the ability of the barrier leg cuffs 32 to reach their full height, and provide the best possible containment.

The aforementioned ranges of included angles are judged suitable for a diaper 20 fitting a range of infant wearers having a weight of 5 to 28 pounds. The angular relationship of the transverse partition 38 relative to the topsheet 24 is measured according to the disclosure of commonly assigned U.S. patent application Ser. No. 08/664,603, filed Jun. 18, 1996 in the names of Roe et al., the disclosure of which is incorporated herein by reference.

Method of Making Absorbent Article With Transverse Barrier

Figure 7:
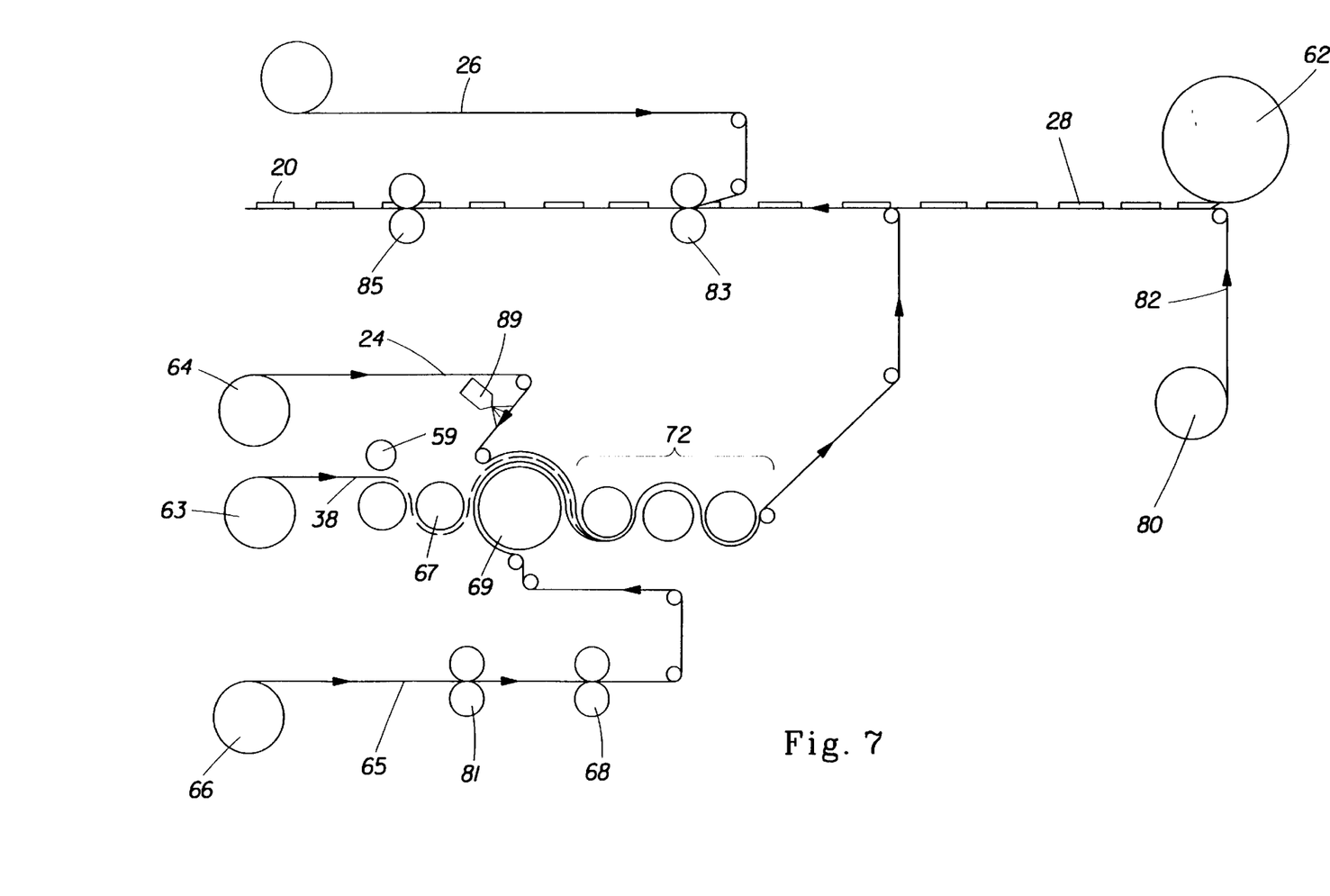
FIG. 7 is a perspective view of one method for making the diaper having a transverse partition.

The diaper 20 of the present invention may be made by the process generally shown in FIG. 7. However, it should be noted that any element of the diaper 20 may be made by any other methods known in the art, including hand-making. Further, any element or elements of the diaper 20 may be manufactured off-line and combined in any stage of their manufacture with the other elements of the diaper 20 on-line. For simplicity, the following process description discloses a preferred method of making the diaper 20 of the present invention which includes making the individual elements of the diaper 20 in parallel with each other on a single line.

As shown in FIG. 7, the barrier leg cuff material 65 is unwound from roll 66. (The barrier leg cuff material 65 may be made on-line or off-line.) In one preferred embodiment, the barrier leg cuff material 65 is provided as a uniform width strip of material as shown in FIG. 6 and then activated such that the material is extensible and/or elastically extensible in at least the desired regions. In this embodiment, cost of manufacture of the diaper 20 may be decreased, for example, by eliminating scrap material that may be cut away from the cuff material in order to provide proper spacing between the distal edges 48 of the barrier cuffs in the crotch region 35 as well as the waist regions 31 and 33. In addition, if the barrier uniform width barrier cuff material 65 is activated after it is attached to the web, the material 65 may be more easily registered with the web in the manufacturing process of the diaper 20.

The barrier leg cuff material 65 is preferably activated so as to provide the leg cuffs 32 with extensibility in the machine direction. The machine direction activation device 81 may be any device known in the art capable of activating the barrier leg cuff material 65 to give machine direction extensibility. In one preferred embodiment, the machine direction activation device 81 includes a stamping or ring rolling device as described in greater detail below with regard to the lateral activation device 68.

Once the barrier leg cuff material 65 has been activated in the machine direction, it is fed into a lateral activation device 68. The lateral activation device 68 activates at least a portion of the leg cuff material 65 in at least the cross-machine direction so as to provide at least a portion of each barrier leg cuff 32 with extensibility in the crossmachine direction. (As used herein, the term "lateral direction" refers to the cross machine direction which is generally perpendicular to the longitudinal centerline L of the diaper.) It should be understood, however, that both leg cuffs 32 need not be activated. Further, the entire leg cuff 32 need not be activated in the lateral direction. For example, as shown in FIGS. 5 and 6, it may be desirable to activate only a portion of each leg cuff 32. In one preferred embodiment, only a portion of each barrier leg cuff 32 is activated to form an activated region 50. Although the activated region 50 can be of any size or shape and can be in any location on the cuff, it is preferred that the activated region 50 correspond with at least a portion of the crotch region 35 and more preferably with at least a portion of the transverse partition 38.

The lateral activation device 68 may be any device known in the art which can provide the material with extension in at least the cross-machine direction. For example, the lateral activation device 68 may ring roll or stamp the material between rollers or plates with corresponding teeth and grooves as further described in U.S. Pat. No. 5,156,793 entitled "Method for Incrementally Stretching Zero Strain Stretch Laminate Web in a Non-Uniform Manner to Impart a Varying Degree of Elasticity Thereto" issued to Buell, et al. on Oct. 20, 1992; U.S. Pat. No. 5,167,897 entitled "Method for Incrementally Stretching a Zero Strain Stretch Laminate Web to Impart Elasticity Thereto" issued to Weber, et al. on Dec. 1, 1992; and U.S. Pat. No. 5,518,801 entitled "Web Materials Exhibiting Elastic-Like Behavior" issued to Chappell, et al. on May 21, 1996; all of which are incorporated by reference herein. In yet other embodiments, the leg cuff material 65 may be activated by methods such as adding elastics in tensioned condition, slitting or folding the material. Also, elastic may be operatively associated in relaxed condition and contracted by known means such as, for example, heat, light, ultrasound etc., to provide extensibility. Any other known method for providing extension and preferably elastic extension characteristics may also be used.

After the barrier leg cuff material 65 has been activated, it is tensioned, aligned and joined to the transverse barrier 38. It should be noted, however, that one or both of the barrier leg cuffs 32 may be activated in the activated region 50 subsequent to the step of joining the transverse partition 38 to the cuffs. The transverse barrier 38 may be supplied from an unwind roll 63 and then cut into individual transverse barrier members 38 which are slipped into place adjacent the barrier leg cuff material 65. (The cut and slip unit for the transverse barrier web is designated 59 in FIG. 7.) Alternatively, the transverse barrier 38 may be supplied to the process already as a prefabricated individual member which is slipped into place adjacent the barrier leg cuff material 65.

In one preferred embodiment, as shown in FIGS. 6–7, the transverse partition 38 is joined to at least one of the barrier leg cuffs 32 adjacent the activated region 50. It is preferred that at least a portion of the transverse barrier 38 adjacent the transverse barrier distal edge 42 is joined to one of the barrier leg cuffs 32. Further, at least one of the barrier leg cuffs 32 is preferably extended in at least the transverse direction when the transverse partition 38 is added. The extension may be done by any known stretching device 69, one example of which is described in more detail in U.S. Pat. No. 5,407,507 entitled "Method and Apparatus for Combining a Tensioned Elastic Member with a Moving Substrate Web", issued to Walter Ball on Apr. 18, 1995. Extending the barrier leg cuff helps to ensure that the transverse partition 38 will stand up away from the topsheet 24 when the diaper 20 is worn, thus providing better restraint of feces flow toward the genitals.

As described above, in one preferred embodiment the lines of attachment 44 joining the barrier leg cuffs 32 with the transverse barrier 38 diverge as one of the waist margins is approached. Preferably, the lines of attachment 44 diverge toward what will be the front of the diaper, although such an arrangement is not necessary. The method of joining the barrier leg cuffs 32 with the transverse barrier 38 may be any known method. (In FIG. 7, the joining device is designated 67.) Suitable joining methods include heat sealing, adhesive joining, ultrasonic welding, sewing and autogenous bonding. A preferred autogenous bonding technique is disclosed in commonly assigned U.S. Pat. No. 4,919,738, issued Apr. 24, 1990 to Ball et al., the disclosure of which is incorporated herein by reference.

Any suitable joining means may be used to join the topsheet 24 and the transverse barrier 38, including, but not limited to those described herein with regard to joining the barrier leg cuffs 32 to the transverse barrier 38. Further, although FIG. 7 shows the barrier leg cuff material 65 being joined to the transverse barrier 38 prior to joining the topsheet 24, alternative embodiments of the present invention are contemplated having a different sequence of steps. For example, the transverse partition 38 may be joined to the barrier leg cuffs 32 after the leg cuffs 32 have been joined to the topsheet 24 or the barrier leg cuffs 32 may be joined to the transverse barrier 38 after the transverse barrier 38 has been joined to the topsheet 24.

The topsheet 24 of the diaper 20 is preferably joined to the barrier leg cuff material 65 and the transverse barrier 38. As shown in FIG. 7, the topsheet 24 is preferably unwound from roll 64 before it is directed to the joining device 72 which joins the barrier leg cuffs 32 to the topsheet 24. The joining device 89 provides a means for joining the transverse barrier 38 to the topsheet 24, such as a glue bead or other known joining means. The topsheet 24 is preferably joined with the transverse barrier 38 adjacent at least a portion of the transverse barrier proximal edge 43. (In FIG. 6, the line of attachment between the topsheet and the transverse barrier 38 is designated 45.)

At least a portion of the cuff 32 adjacent the proximal edge 46 of the cuff 32 is joined to the topsheet 24. Further, at least a portion of the distal edge 48 of the cuff 32 is not joined to any underlying structure. This configuration permits the distal edge 48 of the barrier leg cuff 32 to stand up away from the topsheet 24 in at least a portion of the crotch region 35. Further, at least a portion of each barrier leg cuff 32 is preferably joined adjacent its distal edge 48 in at least a portion of the front and rear regions 31 and 33. This helps to ensure that the cuffs 32 stand up and contain waste rather than flipping out and allowing the urine or feces to leak out of the diaper 20. As shown in FIG. 7, the barrier leg cuff material 65 is joined to the topsheet 24 by the joining device 72. Suitable joining methods include heat sealing, adhesive joining, ultrasonic welding, sewing and autogenous bonding.

The absorbent core 28 of the diaper 20 is formed by the core forming device 62 on a substrate 82 which is unwound from roll 80. The web including the combination of the barrier leg cuff material 65, the transverse barrier 38 and the topsheet 24 is directed adjacent the body-facing surface of the core 28. Once the core 28 is aligned properly with respect to the barrier leg cuffs 32 and the transverse barrier 38, the backsheet 26 is brought in contact with the garment-facing surface of the core 28. (It should be noted that this step can take place before or after other elements of the diaper 20 are joined to the topsheet 24 or the backsheet 26.) Preferably, at least a portion of the topsheet 24 is joined to the backsheet 26 by the joining device 83. Any known method for joining the topsheet 24 and the backsheet 26 may be used, including but not limited to adhesive, pressure, heat, ultrasound or the like. In one preferred embodiment, the topsheet 24 and backsheet 26 are joined in the periphery of the diaper 20, however, other portions of the topsheet 24 and backsheet 26 may be joined. Further, either the topsheet 24, the backsheet 26 or both may be joined to the core 28 or other elements of the diaper 20, such as the leg cuffs 32.

Finally, the diaper web is cut into individual diapers 20 which can be further manipulated or added to before being packaged and shipped. In FIG. 7, the diaper web cutting device is designated 85.

The above-described process is only one of many suitable methods for making the diaper of the present invention. The methods are not intended to limit the scope of the invention. It should also be understood that the preceding steps can be performed in any suitable order and by any suitable method or means. Further, any element of the diaper 20 may be produced off-line or incorporated into the diaper 20 during an off-line process. Thus, while particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for making an absorbent article having a transverse partition, the method comprising the following steps:
    a) providing a first web of barrier leg cuff material in a machine direction, said first web of barrier leg cuff material having a generally uniform width;
    b) providing a second web of barrier leg cuff material in said machine direction, said second web of barrier leg cuff material being generally parallel to said first web of barrier leg cuff material;
    c) activating at least a portion of said first web of barrier leg cuff material so as to provide an activated region which is extensible in at least a lateral direction;
    d) providing a transverse partition having a proximal edge and a distal edge;
    e) joining at least a portion of said transverse partition adjacent said distal edge to said first web of barrier leg cuff material adjacent said activated region of said first web of barrier leg cuff material;
    f) providing a third web of topsheet material;
    g) joining at least a portion of each of said first and second webs of leg cuff material to said third web of topsheet material;
    h) providing a fourth web including an absorbent material disposed on a backsheet material;
    i) joining said third web of topsheet material to said fourth web to form a diaper web; and
    j) cutting said diaper web into individual absorbent articles.

2. The method of claim 1 wherein said activated region is elastically extensible in at least said lateral direction.

3. The method of claim 1 further comprising the steps of activating at least a portion of said second web of barrier leg cuff material adjacent said activated region so as to provide a second activated region which is extensible in at least a lateral direction; and joining at least a portion of said transverse partition adjacent said distal edge to said second web of barrier leg cuff material adjacent said second activated region of said second web of barrier leg cuff material.

4. The method of claim 1 wherein said step of activating said first web of barrier leg cuff material includes ring-rolling said material.

5. The method of claim 1 wherein said step of activating said first web of barrier leg cuff material includes stamping said material.

6. The method of claim 1 wherein said first web of barrier leg cuff material is in a laterally elastically extended condition when said transverse partition is joined to said first web of barrier leg cuff material so as to provide tension to keep said transverse partition taut when said individual absorbent article is fitted to a wearer.

7. The method of claim 1 wherein at least a portion of both said first and said second webs of barrier leg cuff material are activated.

8. The method of claim 1 wherein both said first and said second webs of barrier leg cuff material are activated throughout their entire length.

9. The method of claim 1 wherein at least a portion of said proximal edge of said transverse partition is joined with said third web of topsheet material.

10. The method of claim 1 wherein at least a portion of said first and said second webs are joined to said backsheet.

11. A method for making an absorbent article having a transverse partition, the method comprising the following steps:
    a) providing a first web of barrier leg cuff material in a machine direction, said first web of barrier leg cuff material having a generally uniform width;
    b) providing a second web of barrier leg cuff material in said machine direction, said second web of barrier leg cuff material having a generally uniform width and being generally parallel to said first web of barrier leg cuff material;

c) activating at least a portion of each of said first and said second webs of said barrier leg cuff material so as to provide each said web with an activated region which are each extensible in at least a lateral direction;

d) extending said activated region of at least one of said first and said second webs of barrier leg cuff material in said lateral direction;

e) providing a transverse partition having a proximal edge and a distal edge;

f) joining at least a portion of said transverse partition adjacent said distal edge to each of said first and said second webs of barrier leg cuff material adjacent said activated region while said at least one of said first and second webs of barrier leg cuff material is extended in said lateral direction;

g) providing a third web of topsheet material;

h) joining at least a portion of each of said first and second webs of leg cuff material to said third web of topsheet material;

i) providing a fourth web including an absorbent material disposed on a backsheet material;

j) joining said third web of topsheet material to said fourth web to form a diaper web; and k) cutting said diaper web into individual absorbent articles.

12. The method of claim 11 wherein said activated region is elastically extensible in at least said lateral direction.

13. The method of claim 11 wherein said step of activating said first and second webs of barrier leg cuff material includes ring-rolling said material.

14. The method of claim 11 wherein said step of activating said first and second webs of barrier leg cuff material includes stamping said material.

15. The method of claim 11 wherein both said first and said second webs of barrier leg cuff material are laterally extended when said transverse partition is joined thereto so as to provide tension to keep said transverse partition taut when said individual absorbent article is fitted to a wearer.

16. The method of claim 11 wherein both said first and said second webs of barrier leg cuff material are activated throughout their entire length.

17. The method of claim 11 wherein at least a portion of said proximal edge of said transverse partition is joined with said third web of topsheet material.

18. The method of claim 11 wherein at least a portion of said first and said second webs are joined-to said backsheet.

* * * * *